(12) United States Patent
Pick et al.

(10) Patent No.: US 10,099,930 B2
(45) Date of Patent: Oct. 16, 2018

(54) METHOD FOR THE PRODUCTION OF CARBON NANOTUBE STRUCTURES

(71) Applicant: Q-Flo Limited, Nottingham (GB)

(72) Inventors: Martin Pick, Doncaster (GB); Fiona Ruth Smail, Cambridge (GB); Adam Boies, Cambridge (GB); Christian Hoecker, Cambridge (GB)

(73) Assignee: Q-Flo Limited, Nottingham (GB)

( * ) Notice: Subject to any disclaimer, the term of this patent is extended or adjusted under 35 U.S.C. 154(b) by 0 days.

(21) Appl. No.: 15/532,649

(22) PCT Filed: Dec. 3, 2015

(86) PCT No.: PCT/GB2015/053692
§ 371 (c)(1),
(2) Date: Jun. 2, 2017

(87) PCT Pub. No.: WO2016/087857
PCT Pub. Date: Jun. 9, 2016

(65) Prior Publication Data
US 2017/0327378 A1    Nov. 16, 2017

(30) Foreign Application Priority Data
Dec. 5, 2014   (GB) .................................. 1421664.2

(51) Int. Cl.
| | | |
|---|---|---|
| *C01B 32/162* | (2017.01) | |
| *C07C 9/04* | (2006.01) | |
| *C07F 15/02* | (2006.01) | |
| *C07D 333/10* | (2006.01) | |
| *C07C 13/00* | (2006.01) | |
| *C01B 32/72* | (2017.01) | |
| *C07C 11/00* | (2006.01) | |
| *C07C 9/00* | (2006.01) | |

(Continued)

(52) U.S. Cl.
CPC .............. *C01B 32/162* (2017.08); *C07C 9/04* (2013.01); *C01B 32/72* (2017.08); *C07C 9/00* (2013.01); *C07C 11/00* (2013.01); *C07C 13/00* (2013.01); *C07C 15/00* (2013.01); *C07D 333/10* (2013.01); *C07F 15/02* (2013.01); *C07F 17/02* (2013.01)

(58) Field of Classification Search
CPC ......... C01B 32/162; C01B 32/72; C07C 9/04; C07C 9/00; C07C 11/00; C07C 13/00; C07C 15/00; C07D 333/10; C07F 15/02; C07F 17/02
See application file for complete search history.

(56) References Cited

U.S. PATENT DOCUMENTS

| | | | | |
|---|---|---|---|---|
| 6,761,870 B1* | 7/2004 | Smalley | ..................... | B01J 3/04 423/445 R |
| 2006/0104888 A1* | 5/2006 | Higashi | .................. | B82Y 30/00 423/447.3 |

(Continued)

FOREIGN PATENT DOCUMENTS

WO    WO 2008/132459 A1    9/2008

OTHER PUBLICATIONS

International Search Report, PCT/GB2015/0536952, dated Sep. 3, 2016, 2 pages.

*Primary Examiner* — Daniel C McCracken
(74) *Attorney, Agent, or Firm* — Swanson & Bratschun, L.L.C.

(57) ABSTRACT

The present invention relates to a method for the production of carbon nanotube structures.

15 Claims, 13 Drawing Sheets

(51) Int. Cl.
*C07F 17/02* (2006.01)
*C07C 15/00* (2006.01)

(56) References Cited

U.S. PATENT DOCUMENTS

| | | | | |
|---|---|---|---|---|
| 2007/0148962 | A1* | 6/2007 | Kauppinen | B82Y 30/00 |
| | | | | 438/637 |
| 2008/0107587 | A1* | 5/2008 | Yumura | B82Y 30/00 |
| | | | | 423/447.3 |
| 2010/0260931 | A1 | 10/2010 | Malecki et al. | |
| 2011/0150746 | A1 | 6/2011 | Khodadadi et al. | |
| 2013/0309473 | A1* | 11/2013 | Sundaram | B01J 23/745 |
| | | | | 428/220 |

\* cited by examiner a)

b)

METHOD FOR THE PRODUCTION OF CARBON NANOTUBE STRUCTURES

RELATED APPLICATIONS

This application is a 35 U.S.C. § 371 national phase application of PCT/GB2015/053692 (WO 2016/087857), filed on Dec. 3, 2015, entitled "Method", which application claims priority to United Kingdom Application Serial No. 1421664.2, filed Dec. 5, 2014, which is incorporated herein by reference in its entirety.

The present invention relates to a method for the production of carbon nanotube structures.

Carbon nanotubes (CNTs) are of considerable interest for numerous applications owing to their exceptional nanoscale mechanical, electrical, thermal and chemical properties. However the production of satisfactorily assembled CNT structures on an industrial scale is still to be achieved. Current processes produce a low yield of CNTs with low levels of impurities, a high yield of CNTs with high levels of impurities (>60%) or low throughput.

There are a number of different techniques for assembling individual CNTs into CNT structures. Examples include spinning CNT fibres from a liquid-crystal phase, spinning fibres or pulling a continuous film from forest-grown CNTs. A one-step, continuous gas-phase process which involves spinning a film or fibre from a floating method is currently the most attractive as an industrially scalable route (see for example WO-A-2005/07926). The process involves the continuous, controlled injection of a hydrocarbon source, an iron source (typically ferrocene vapour) and a sulfur source into a tubular reactor at temperatures above 1000° C. in a reducing atmosphere. Thermal decomposition of the iron source leads to the formation of iron nanoparticles which provide a catalytic surface for CNT growth once sufficient carbon is available from the decomposition of the hydrocarbon. As CNTs begin to grow, they preferentially bundle due to Van der Waals forces and these bundles intertwine to form an aerogel. The aerogel is mechanically drawn from the tubular reactor onto a winding mechanism for continuous collection.

Iron nanoparticles form via homogenous nucleation from a saturated vapour phase which is created as the iron source decomposes. Coagulation, surface growth, thermophoresis and diffusion impact on nanoparticle behaviour. The growth rate of the iron nanoparticles is difficult to predict as there are more than one reactant species present. There is no available experimental information relating to changes in nanoparticle size along a tubular reactor.

Control of the formation of catalyst nanoparticles is widely recognized as a key parameter in controlling the diameter, purity, yield, crystalline quality, entanglements, chirality and number of walls of the CNTs in the CNT structure and therefore in optimizing the bulk material properties. The diameter of the catalyst nanoparticle correlates closely with the diameter of the CNT. However in some CVD systems only 1% of iron based nanoparticles lead to CNT growth. The additional iron contributes to the co-synthesis of undesirable impurities such as graphitically encapsulated nanoparticles, defective nanotubes and large diameter carbon tubules. The impurities are enmeshed in the CNT aerogel and disrupt the mechanical and electrical properties of the CNT structure.

The synthesis of CNT structures can additionally be influenced by parameters such as the choice of reagents and their ratios. Although control of the quantity of the sulphur source is crucial, the precise role of sulfur is still under investigation. Current research suggests that sulphur plays a role in conditioning the iron nanoparticles by changing the solubility of the carbon at the surface and hence accelerating CNT growth.

The present invention is based on the surprising recognition that particulate metal catalyst is generated in discrete zones of a temperature-controlled flow-through reactor. This is exploited to improve production of CNT structures by controlling the flow of a source of carbon and/or the flow of a source of sulphur into the temperature-controlled flow-through reactor to optimise convergence with the discrete zones of particulate metal catalyst.

Thus viewed from a first aspect the present invention provides a method for the production of carbon nanotube structures comprising:

(a) introducing a flow of metal catalyst or metal catalyst precursor into a temperature-controlled flow-through reactor;

(b) exposing the flow of metal catalyst or metal catalyst precursor to a first temperature zone sufficient to generate particulate metal catalyst, wherein the first temperature zone includes a region of peak particle concentration;

(c) releasing an axial or radial flow of a source of carbon into the temperature-controlled flow-through reactor at a release point;

(d) exposing the particulate metal catalyst and source of carbon to a second temperature zone downstream from the first temperature zone, wherein the second temperature zone is sufficient to produce carbon nanotube structures;

(e) exposing the particulate metal catalyst and source of carbon to a third temperature zone downstream from the second temperature zone, wherein the third temperature zone is sufficient to evaporate the particulate metal catalyst;

(f) exposing the particulate metal catalyst and source of carbon to a fourth temperature zone downstream from the third temperature zone, wherein the fourth temperature zone is sufficient to re-nucleate the particulate metal catalyst and to produce carbon nanotube structures; and (g) discharging the carbon nanotube structures from a discharge outlet of the temperature-controlled flow-through reactor, wherein either the release point is substantially between the beginning of the first temperature zone and the end of the second temperature zone or the method further comprises: (f') releasing an axial or radial flow of a source of sulphur into the temperature-controlled flow-through reactor at a release location, wherein the release location is at or near to the fourth temperature zone.

By releasing the source of carbon between the beginning of the first temperature zone and the end of the second temperature zone, the method of the invention facilitates instant convergence between the source of carbon and a discrete zone of high particle concentration to optimise formation of carbon nanotube structures. Similarly by releasing the flow of a source of sulphur into the fourth temperature zone, the method of the invention facilitates instant convergence between the source of sulphur, the source of carbon and a discrete zone of high particle concentration (re-nucleated particles) to optimise formation of carbon nanotube structures and minimise the formation of undesirable by-products.

In a preferred embodiment, the release point is substantially between the beginning of the first temperature zone and the end of the second temperature zone and the method further comprises: (f) releasing an axial or radial flow of a source of sulphur into the temperature-controlled flow-through reactor at a release location, wherein the release location is at or near to the fourth temperature zone.

Preferably the release point is substantially coincident with the region of peak particle concentration.

Preferably the release location is upstream from and near to the fourth temperature zone.

The temperature-controlled flow-through reactor may be adapted to provide an axial temperature gradient. The axial temperature gradient may be non-uniform (eg stepped). The temperature of the temperature-controlled flow-through reactor may be controlled by resistive heating, plasma or laser.

Preferably the temperature profile in the temperature-controlled flow-through reactor is substantially parabolic.

The first temperature zone sufficient to generate particulate metal catalyst may extend over at least the range 600 to 1100° C. As shown in FIG. 12, the first temperature zone may be in a first reaction chamber 21 of the temperature-controlled flow-through reactor.

The second temperature zone sufficient to produce carbon nanotube structures may extend over at least the range 900 to 1150° C. As also shown ion FIG. 12, the second temperature zone may be in a second reaction chamber 22 of the temperature-controlled flow-through reactor.

The third temperature zone sufficient to evaporate the particulate metal catalyst may extend over at least the range 1150 to 1400° C. As also shown ion FIG. 12, the third temperature zone may be in a third reaction chamber 23 of the temperature-controlled flow-through reactor.

The fourth temperature zone sufficient to re-nucleate the particulate metal catalyst and to produce carbon nanotube structures may extend over at least the range 600 to 1150° C. As also shown ion FIG. 12, the fourth temperature zone may be in a fourth reaction chamber 24 of the temperature-controlled flow-through reactor.

Before step (c), the source of carbon may be heated.

Before step (c), the source of carbon may be subjected to radiative heat transfer by a source of infrared, visible, ultraviolet or x-ray energy.

In step (c), the source of carbon may be released (eg injected) in a linear, axial, vortical, helical, laminar or turbulent flow path.

The temperature-controlled flow-through reactor may be adapted to introduce the source of carbon by an injection nozzle, lance, probe or a multi-orificial injector (eg a shower head injector).

The distance between the point of discharge of the particulate metal catalyst and the release point may be 10 cm or less.

In step (c), the source of carbon may be released at a plurality of release points.

Preferably in step (c), the source of carbon is released in an axial counterflow (eg in an upstream direction). For example, the source of carbon may be released in an axial counterflow through a lance inserted into the temperature-controlled flow-through reactor. Alternatively the source of carbon may be released in an axial counterflow through an internal sleeve on the inside wall of the temperature-controlled flow-through reactor.

The release of the source of carbon in an axial counterflow has the advantage that the source of carbon has passed through the temperature-controlled flow-through reactor and is at an elevated temperature at the release point.

The axial counterflow may be up to 30 l/min.

Preferably in step (c) the source of carbon is released radially (eg substantially in a radial plane). Particularly preferably step (c) is: releasing the source of carbon substantially in a radial plane at a plurality of angles in the range −90° to +90°. The source of carbon may be released radially through one or more radial ports or injection nozzles. For example, the temperature-controlled flow-through reactor may be fitted with a manifold through which the source of carbon is released radially.

The source of carbon may be an optionally substituted and/or optionally hydroxylated aromatic or aliphatic, acyclic or cyclic hydrocarbon (eg alkyne, alkane or alkene) which is optionally interrupted by one or more heteroatoms (eg oxygen). Preferred is an optionally halogenated $C_{1-6}$-hydrocarbon (eg methane, propane, acetylene or tetrachloroethylene), an optionally mono-, di- or tri-substituted benzene derivative (eg toluene) or $C_{1-6}$-alcohol (eg ethanol).

Preferably the source of carbon is methane optionally (but preferably) in the presence of an optionally substituted and/or optionally hydroxylated aromatic or aliphatic, acyclic or cyclic hydrocarbon (eg alkyne, alkane or alkene) which is optionally interrupted by one or more heteroatoms (eg oxygen).

In a preferred embodiment, the source of carbon is methane optionally in the presence of propane or acetylene.

Typically in step (c), the source of carbon is introduced with a carrier gas such as helium, hydrogen or argon.

Typically the particulate metal catalyst is a nanoparticulate metal catalyst.

Preferably the nanoparticles of the nanoparticulate metal catalyst have a mean diameter (eg a number, volume or surface mean diameter) in the range 4 to 15 nm.

Preferably 80% or more of the particles of the nanoparticulate metal catalyst have a diameter of less than 30 nm. Particularly preferably 80% or more of the particles of the nanoparticulate metal catalyst have a diameter of less than 12 nm.

The concentration of the particulate metal catalyst generated in step (b) may be in the range $10^6$ to $10^{10}$ particles $cm^{-3}$.

Typically the metal catalyst is one or more of the group consisting of alkali metals, transition metals, rare earth elements (eg lanthanides) and actinides.

Preferably the metal catalyst is one or more of the group consisting of transition metals, rare earth elements (eg lanthanides) and actinides.

Preferably the metal catalyst is at least one of the group consisting of Fe, Ru, Co, W, Cr, Mo, Rh, Ir, Os, Ni, Pd, Pt, Ru, Y, La, Ce, Mn, Pr, Nd, Tb, Dy, Ho, Er, Lu, Hf, Li and Gd.

Preferably the metal catalyst is iron.

The generation of particulate metal catalyst may be initiated in step (b) by thermal decomposition or dissociation of the metal catalyst or metal catalyst precursor into metal species (eg atoms, radicals or ions). The production of particulate metal catalyst in step (b) may comprise nucleation accompanied by particle growth. The result is clusters of particulate metal catalyst and a wider distribution of particle diameters.

The metal catalyst or metal catalyst precursor introduced in step (a) may be in a gaseous, liquid or solid form. The metal catalyst precursor may be sublimable. Step (a) may be preceded by the step of sublimating the metal catalyst precursor.

The metal catalyst or metal catalyst precursor may be introduced in step (a) with one or more carrier gases. The (or each) carrier gas may be inert or reducing. The (or each) carrier gas may be selected from the group consisting of argon, helium and hydrogen. The mass flow of the metal catalyst or metal catalyst precursor in admixture with the carrier gas is generally in the range 10 to 30 μmin.

The metal catalyst precursor may be a metal complex or organometallic metal compound. Examples include iron pentacarbonyl, ferrocene or a ferrocenyl derivative (eg ferrocenyl sulphide).

Preferably the metal catalyst precursor is sulphur-containing. A metal catalyst precursor which is sulphur-containing may promote carbon nanotube growth.

Preferably the metal catalyst precursor is a sulphur-containing organometallic. Particularly preferably the metal catalyst precursor is a sulphur-containing iron organometallic. More preferably the metal catalyst precursor is a sulphur-containing ferrocenyl derivative. Yet more preferably the metal catalyst precursor is mono-(methylthio) ferrocene or bis-(methylthio) ferrocene.

In a preferred embodiment, the metal catalyst precursor is ferrocene and a sulphur-containing ferrocenyl derivative. This embodiment gives advantageous control over the Fe:S ratio for optimal CNT growth.

The metal catalyst or metal catalyst precursor may be introduced in step (a) together with a sulphur-containing additive. The sulphur-containing additive may promote carbon nanotube growth. The sulphur-containing additive may be thiophene, iron sulphide, a sulphur-containing ferrocenyl derivative (eg ferrocenyl sulphide) or carbon disulphide.

In a preferred embodiment, the metal catalyst precursor is ferrocene optionally together with a sulphur-containing additive being thiophene or carbon disulphide.

The metal catalyst or metal catalyst precursor may be introduced (eg injected) in a linear, axial, vortical, helical, laminar or turbulent flow path. The metal catalyst or metal catalyst precursor may be introduced at a plurality of locations.

Preferably step (a) is: introducing a flow of metal catalyst or metal catalyst precursor axially into the temperature-controlled flow-through reactor (eg at the upstream end of the temperature-controlled flow-through reactor). The metal catalyst or metal catalyst precursor may be introduced axially through a probe or injector (eg a multi-orificial injector such as a showerhead injector).

Preferably step (a) is: introducing a flow of metal catalyst or metal catalyst precursor radially (eg substantially in a radial plane) into the temperature-controlled flow-through reactor. Particularly preferably step (a) is: introducing a flow of metal catalyst or metal catalyst precursor substantially in a radial plane at a plurality of angles in the range −90° to +90° into the temperature-controlled flow-through reactor. The metal catalyst or metal catalyst precursor may be introduced radially through one or more radial ports or injection nozzles. For example, the temperature-controlled flow-through reactor may be fitted with a manifold through which the metal catalyst or metal catalyst precursor is released radially.

The source of sulphur may be thiophene, iron sulphide, a sulphur-containing ferrocenyl derivative (eg ferrocenyl sulphide) or carbon disulphide. The source of sulphur may promote carbon nanotube growth.

In a preferred embodiment, the source of sulphur is thiophene or carbon disulphide.

The source of sulphur may be released in step (f) with a carrier gas such as helium, hydrogen or argon.

The carbon nanotubes may be single-walled and/or multi-walled carbon nanotubes. The carbon nanotube structure may be a fibre, mat, plate, wire, film or a mixture thereof or an intermediate thereof such as a web, agglomerate, aggregate or aerogel.

The temperature-controlled flow-through reactor may be cylindrical. The temperature-controlled flow-through reactor may be substantially vertical or horizontal. Preferably the temperature-controlled flow-through reactor is substantially horizontal.

Preferably the method further comprises measuring the particle size distribution of the particulate metal catalyst in the first temperature zone.

Preferably the method further comprises measuring the particle size distribution of the particulate metal catalyst in the fourth temperature zone.

Preferably the method further comprises measuring the region of peak particle concentration in the first temperature zone of the temperature-controlled flow-through reactor.

The present invention will now be described in a non-limitative sense with reference to Examples and the accompanying Figures in which:

FIG. 1 illustrates the temperature gradients between the wall and centreline of a tubular reactor;

FIGS. 2a-c illustrate FT-IR analysis of the exhaust gases at different temperature set points to show the decomposition behaviour of thiophene and ferrocene alone and together;

Figure 11:
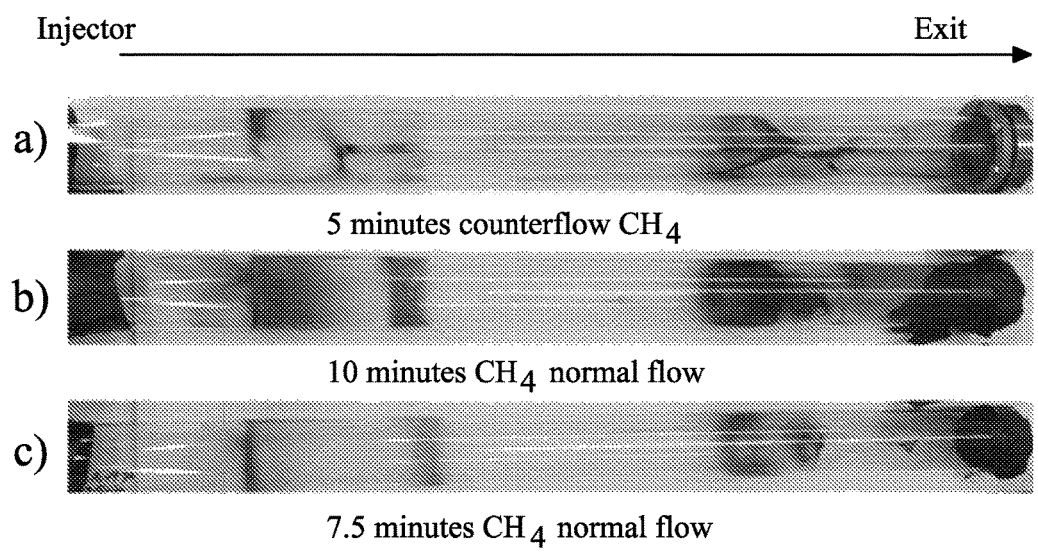
Figure 12:
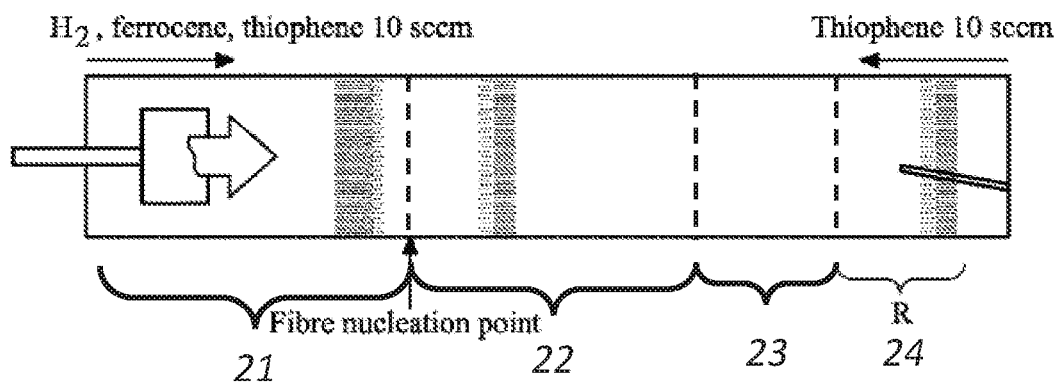
Figure 13:
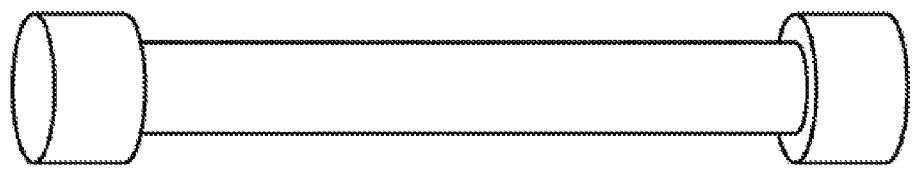
Figure 13:
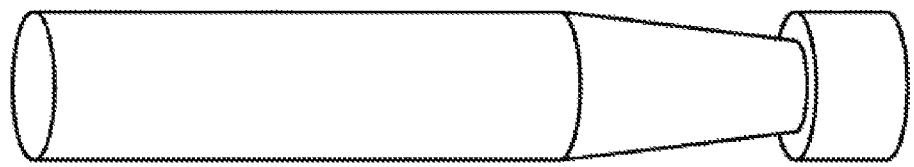

FIGS. 11a-c illustrate results from the embodiment of the method of the invention compared with the conventional method;

FIG. 12 illustrates schematically an embodiment of the method of the invention; and FIGS. 13a-b illustrate various multi-diameter discharge outlets of the tubular reactor.

EXAMPLE 1

Experimental

Figure 7:
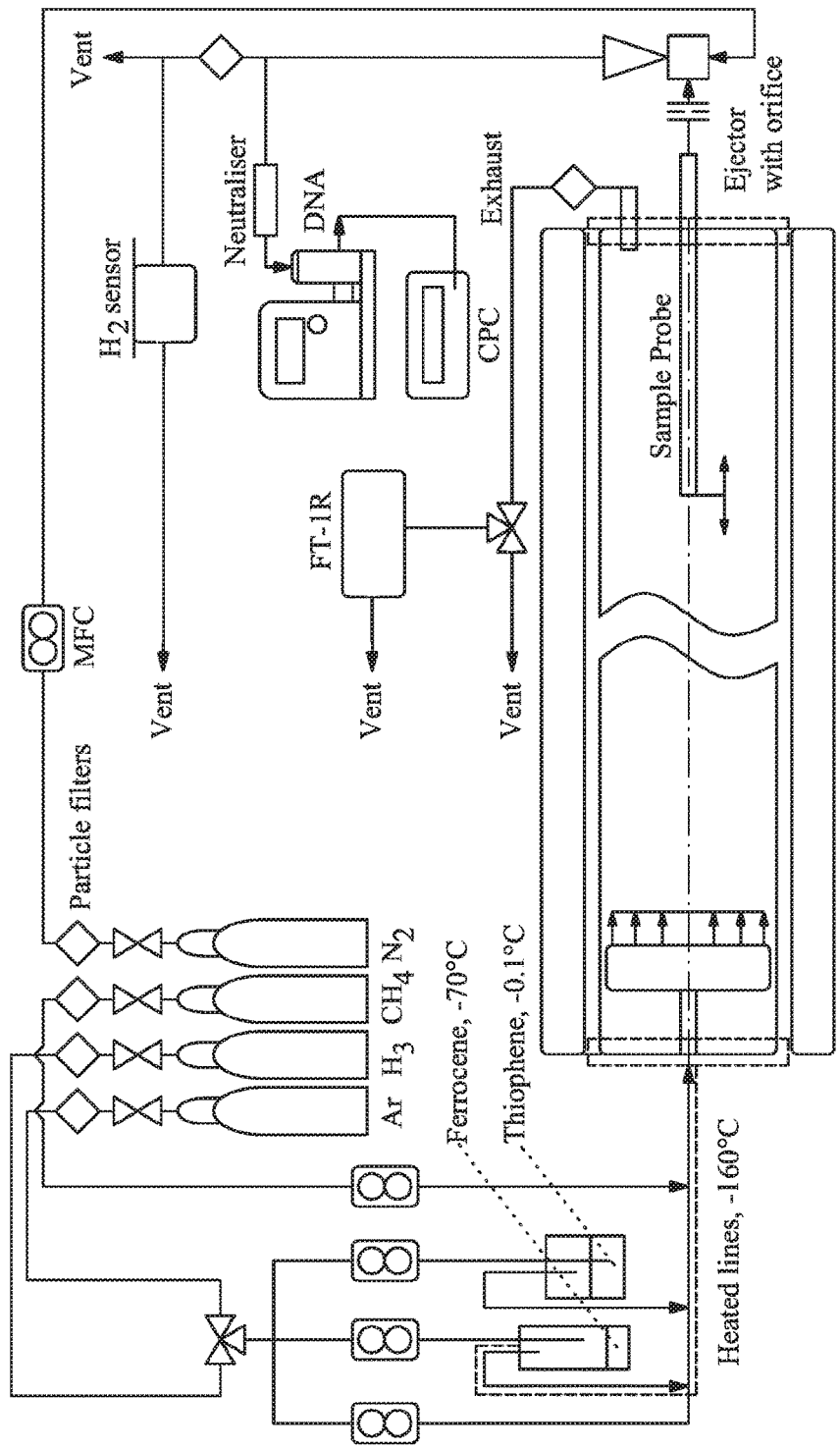
FIG. 7 illustrates schematically the experimental set-up used in Example 1.
Figure 8:
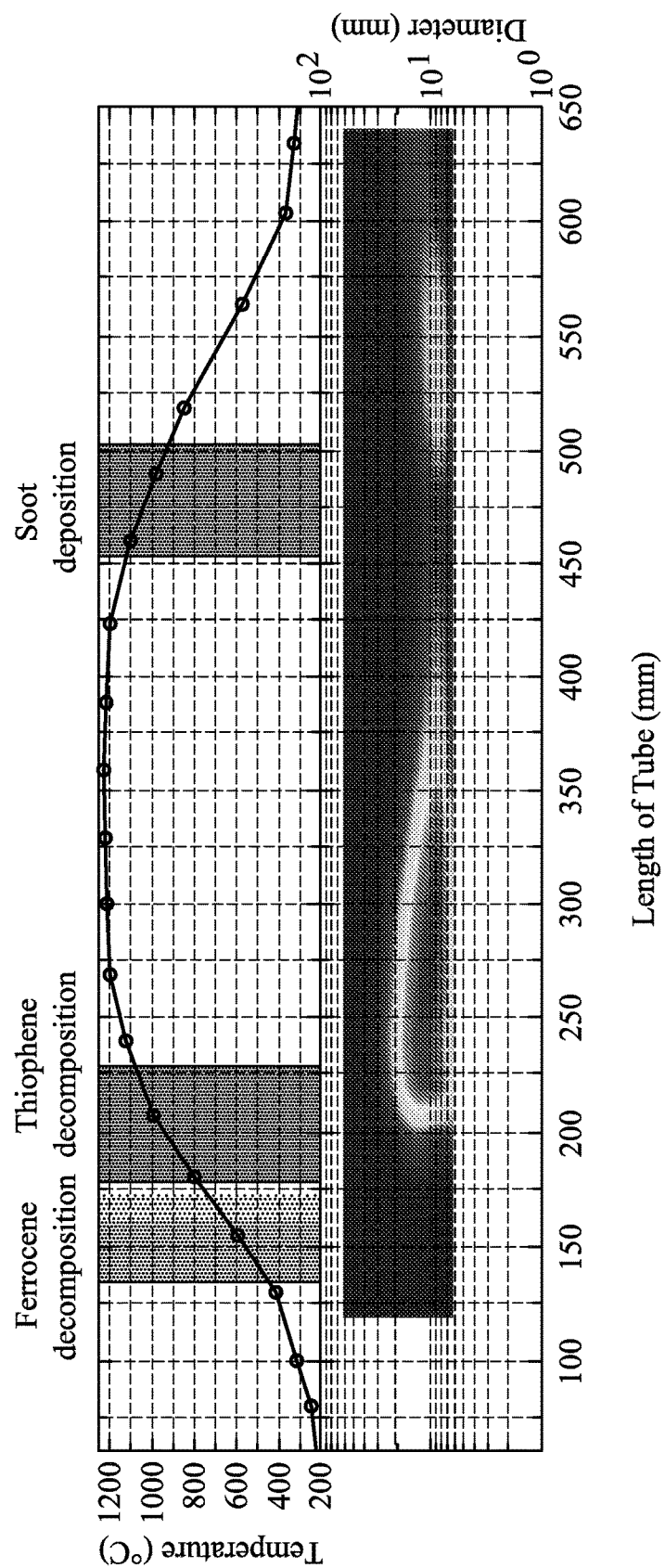
FIG. 8 illustrates particle size distribution, decomposition and deposition along the tubular reactor at a set point of 1200° C.

Experiments were carried out in a horizontal tubular reactor in ambient conditions and at variable temperatures. A schematic of the experimental setup is shown in FIG. 7. A sampling system was used to extract catalyst particles from axial locations and information was taken from velocity and thermal profiles and from axial analysis of carbon species synthesized from the particles.

A bulk flow of 0.5 slpm hydrogen (purity grade hydrogen N5.0 (BOC)) carrying ferrocene (~2 wt %) and thiophene (~0.3 wt %) entered the tubular reactor (40 mm ID and 700 mm length) through a showerhead injector. This ensured a uniform and laminar inflow with typical Re~25<<2300 at the inlet. Flow rates were controlled by mass flow controllers (Alicat). The injector face was placed 70 mm from the inlet of the tubular reactor which was below 400° C. to avoid decomposition of ferrocene in the injector.

Particle measurements were carried out in situ by means of a TSI-Scanning Mobility Particle Sizer 3080 (SMPS) system including a TSI-Ultrafine Condensation Particle Counter 3776 (UCPC) and TSI-Differential Mobility Analyzers 3081 and 3085 (DMA) in an alumina (basis 99% $Al_2O_3$) tubular reactor. Samples along the centreline were taken through a 1.9 mm ID alumina probe at flow rates inside the probe of 0.300-0.450 slpm and were assisted by an ejector system including a 16/1000 inch orifice. Typically this was implemented at the end of the probe by a 1:50 dilution with pure and filtered ambient temperature nitrogen. The data presented was corrected for dilution, diffusion and thermophoretic losses in the probe. Exhaust gases were vented to atmosphere through a low pressure drop HEPA filter.

FT-IR was used to analyze gases along the axis of the tubular reactor and in the exhaust. The sampler for the FTIR was located in the hottest part of the tubular reactor and the set temperature was sequentially raised and the effect on the IR spectrum was recorded. This allowed the detection of the onset of (for example) ferrocene or thiophene decomposition and of the temperature at which complete decomposition occurred.

In a further configuration, methane was introduced at 0.06 slpm to serve as a source of carbon for carbon nanotube growth. Optical access was gained by using a quartz tubular reactor at 1200° C. and performing a rapid shut down of all reactant gases while allowing the experiment to cool down in an argon (99.998% (BOC)) atmosphere. The morphology of the carbon nanotube web that formed was then investigated by means of scanning electron microscopy (SEM).

Results and Discussion

Flow Dynamics

Figure 1:
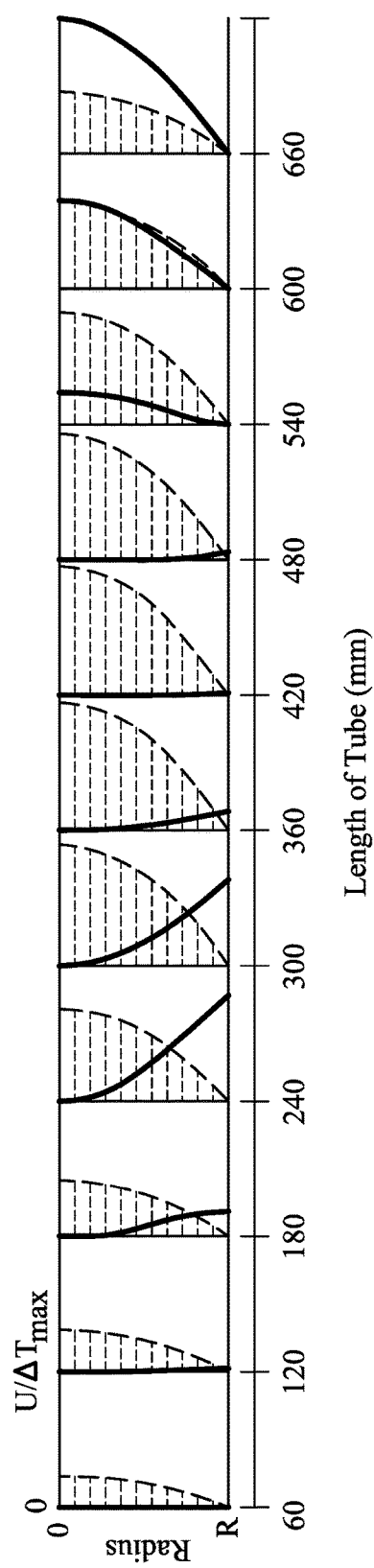

The gas velocity inside the tubular reactor and along its axis varies according to the ideal gas law. This means that the centreline velocity increases with increasing temperature. Conservation of mass, momentum and energy are taken into account in a 2D axisymmetric reactor model. Since the concentration of ferrocene and thiophene in the hydrogen bulk flow is very low, it can be ignored and its dynamics are decoupled from fluid dynamics. In a simulation of the flow dynamics within the tubular reactor, a uniform inflow, a temperature profile as shown in FIG. 1 at the outside wall of the tubular reactor and atmospheric pressure are assumed. Because of a no slip condition at the wall, the gradient of velocity increases along the tubular reactor until the temperature decreases beyond the mid-point which results in greater shear within the flow. The contribution of CNTs to viscous forces are omitted but may play an important role in the velocity profile. No radiative heat transfer between CNTs and the wall is taken into account.

Figure 6:
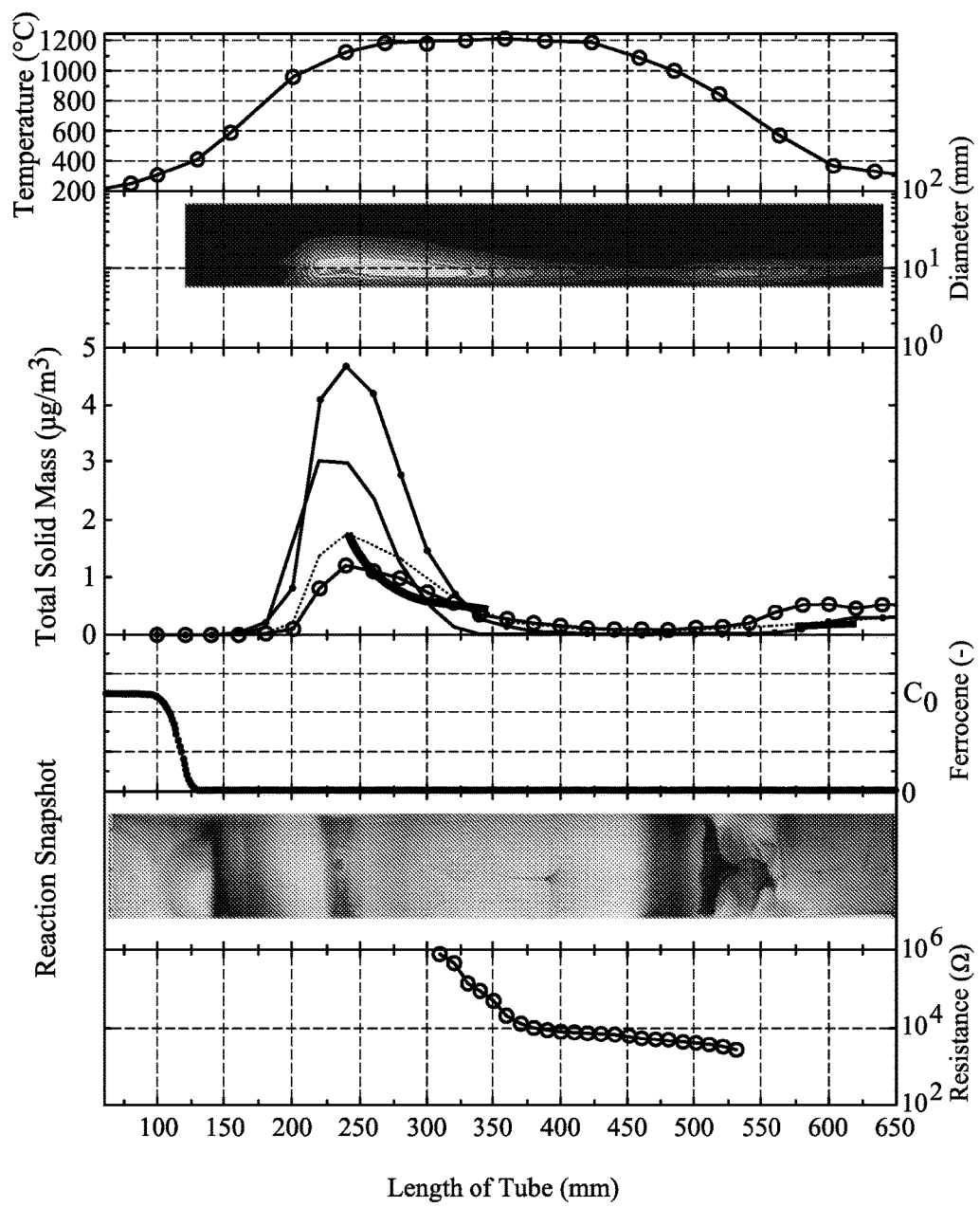
FIG. 6 illustrates the temperature profile at a set point of 1200° C., a particle size distribution measured at that set point along the tubular reactor, modelling results of particle growth and ferrocene decomposition, a reaction snapshot and a resistance measurement.

A parabola shaped temperature profile is present in the tubular reactor (see FIG. 6). The actual temperature in the gas flow almost follows this profile. The radial temperature gradient illustrated in FIG. 1 at different locations within the tubular reactor represents the thermal diffusivity of energy from the walls into the tubular reactor. The gradient in temperature at the centreline is $dT/dr|_{r=0}$>0 until x≈480 mm and becomes negative for x>480 mm. Unlike the velocity gradient, the gradient in temperature is at a minimum near the hottest region of the tubular reactor and at a maximum near the entry and exit of the tubular reactor. Given the temperature gradients between wall and centreline, thermophoretic forces drive particles away from the wall when $dT/dr$>0 for x<480 mm and towards the wall when $dT/dr$<0 for x>480 mm.

Decomposition of Ferrocene and Thiophene

Figure 2A:
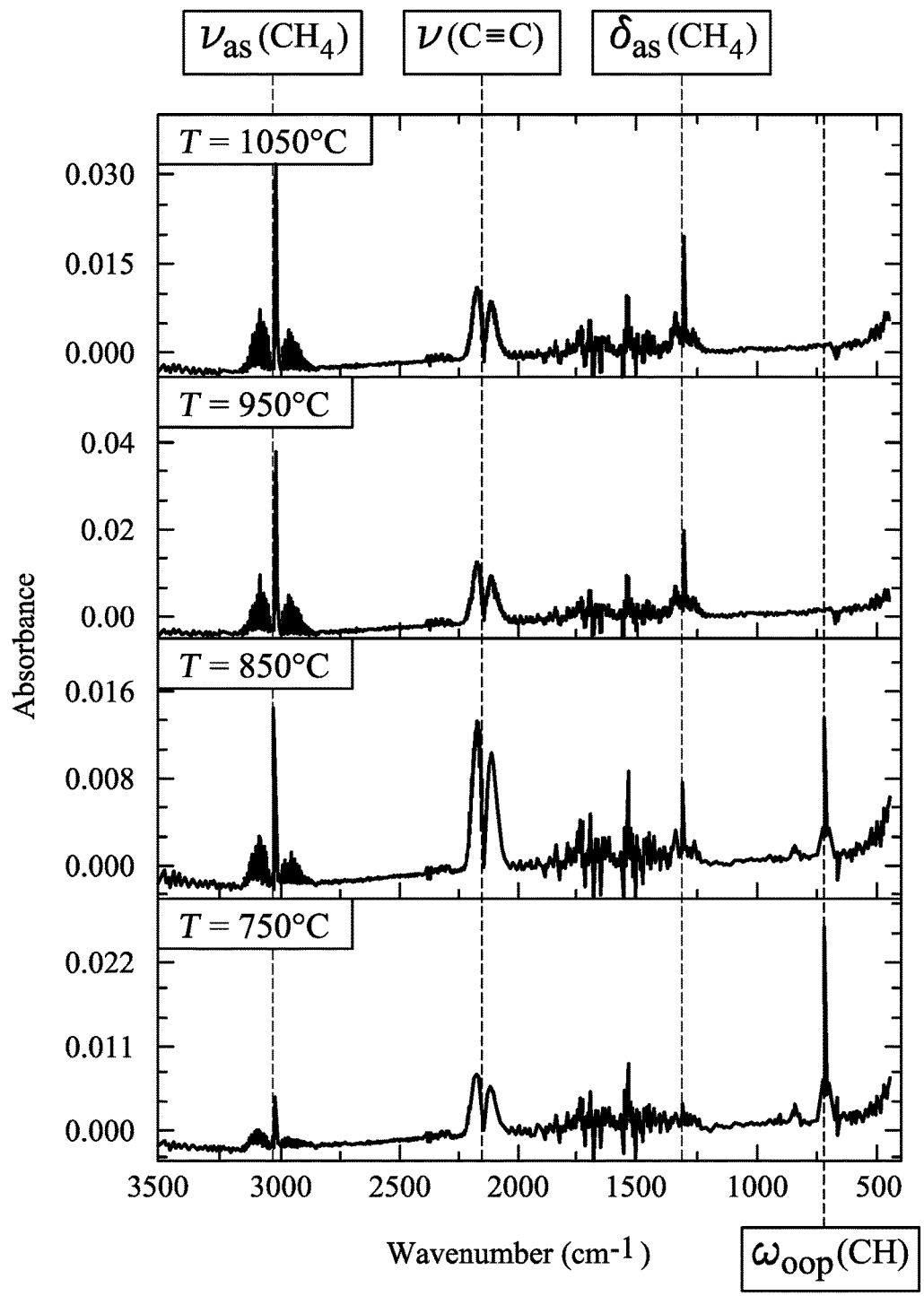
Figure 2B:
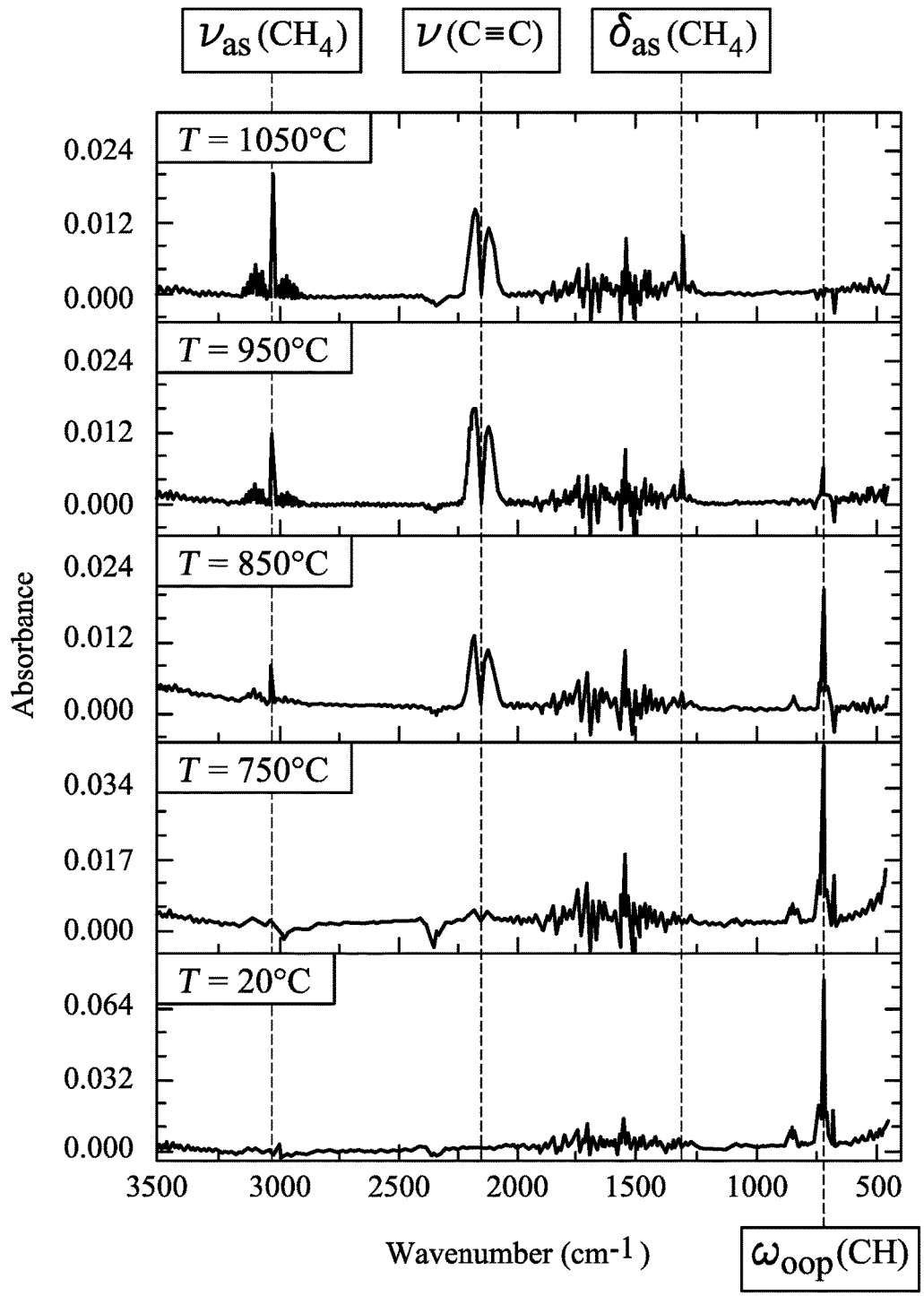
Figure 2C:
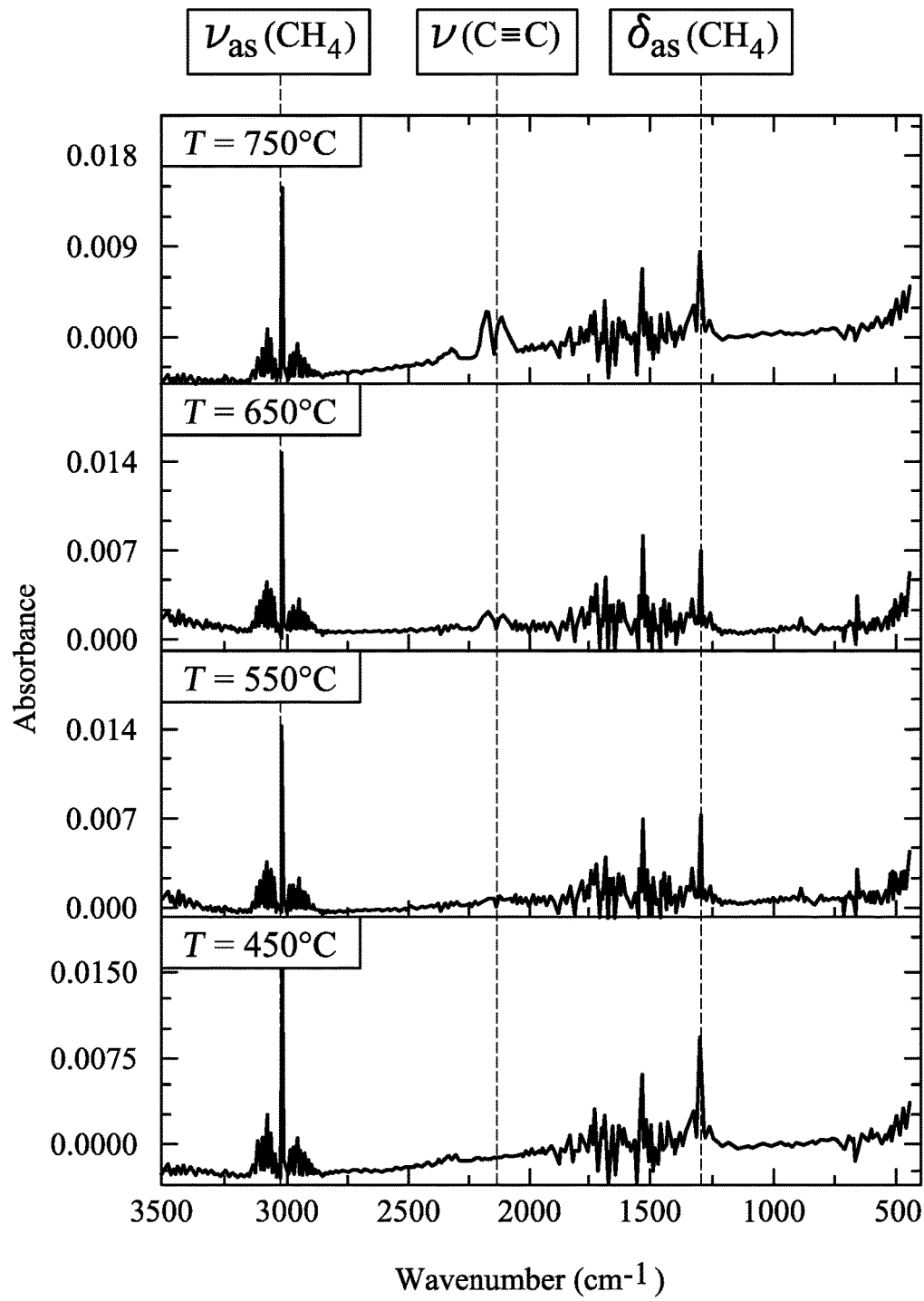

FT-IR analyses of the exhaust gases at different temperature set points showed the decomposition behavior of thiophene and ferrocene alone and together (see FIGS. 2a-c).

For thiophene entering the tubular reactor alone, a $CH_4$ mode and a C-triple bond mode appeared in the IR spectra as the temperature increased. This indicated thiophene decomposition. In addition, the appearance of a CH bending mode indicated that thiophene was disappearing as the temperature increased. Decomposition started at a set point of ~750° C. and was complete at a set point of ~1050° C.

For ferrocene entering the tubular reactor alone, the appearance of a C-triple bond mode indicated ferrocene decomposition at a set point of ~550° C. which reached its maximum at ~750° C.

For thiophene and ferrocene entering the tubular reactor together, the disappearance of the CH bending mode was independent of the presence of ferrocene. At ~750° C., a C-triple bond mode was already present indicating that ferrocene had already been decomposed. The intensity of the C-triple bond and $CH_4$ mode increased as temperature increased which indicated that thiophene was decomposing.

Figure 5:
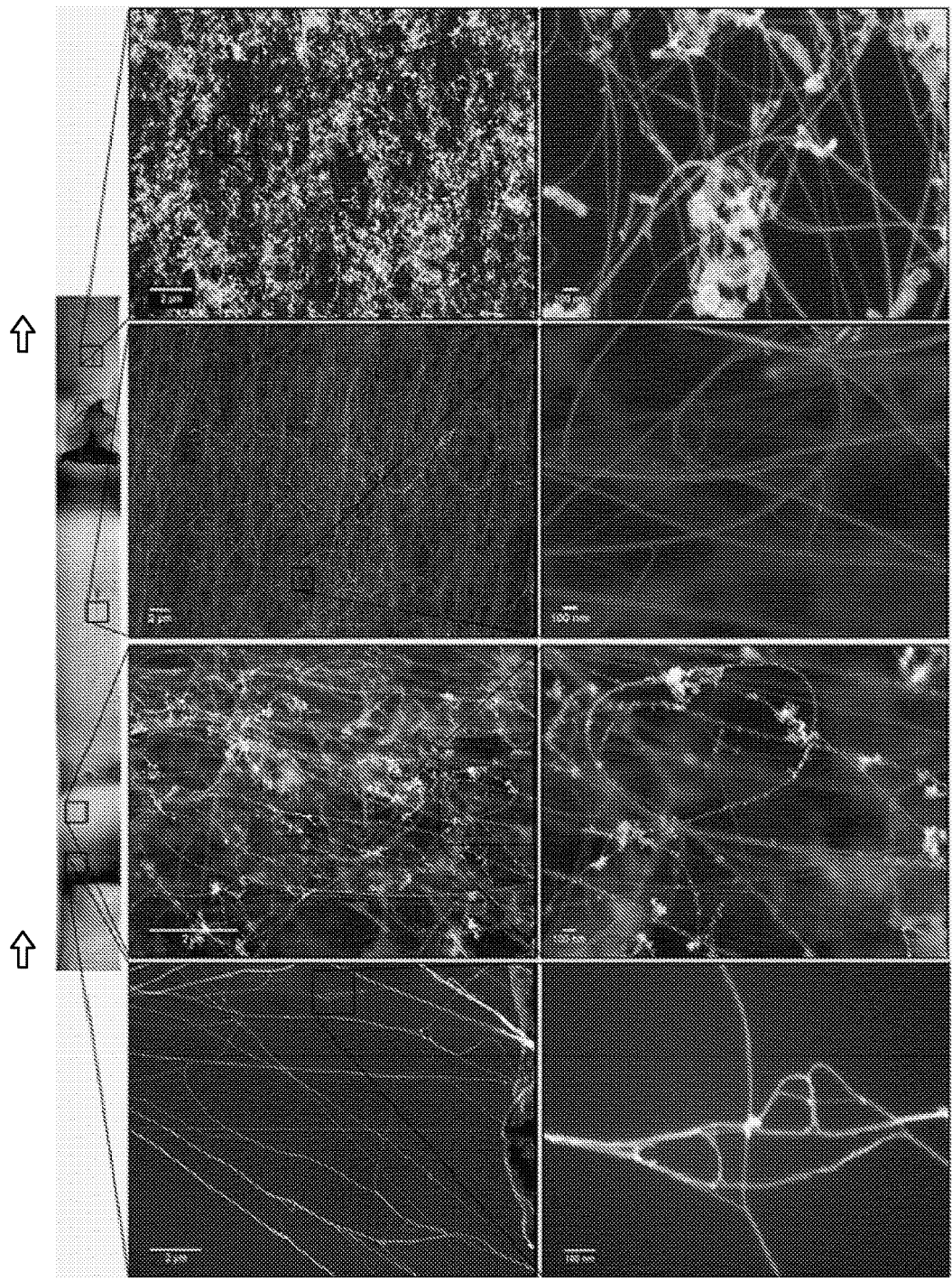
FIG. 5 illustrates scanning electron microscopy (SEM) images showing different morphologies of the CNT fibre along the axis of the tubular reactor.
Figure 9:
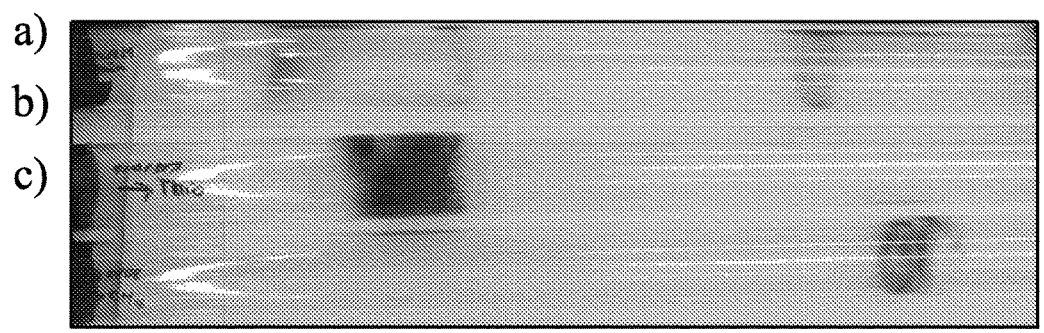
FIG. 9 illustrates different reactants in the tubular reactor at 1200° C., namely a) ferrocene, thiophene and methane (5 minute run); b) thiophene; and c) methane.

Deposits of iron and soot on the tubular reactor wall in the respective temperature zones were observed (see FIG. 9). The deposition and therefore decomposition of reactants are mutually independent and can be detected for each species individually. Alongside the thermal experiments, it is clear that ferrocene and thiophene are a source of carbon for CNT nucleation (see FIGS. 5 and 6).

Particle Size Distributions

Figure 3:
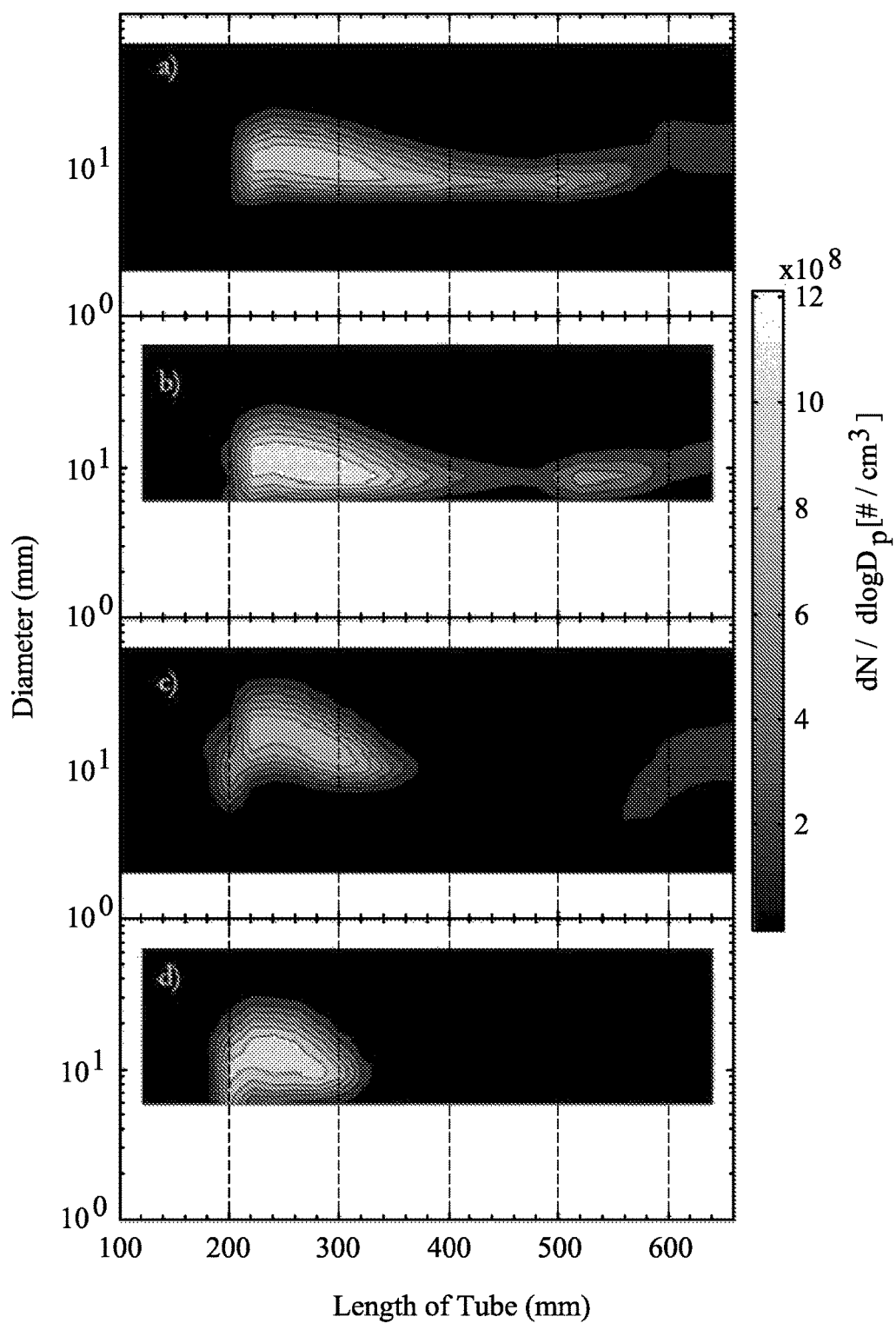
FIG. 3 illustrates TSI-Scanning Mobility Particle Sizer 3080 (SMPS) measurements of particle size distribution in the tubular reactor.

Axial measurement of particle size distributions along the centreline of the tubular reactor in the absence of methane showed almost instantaneous nucleation of catalyst nanoparticles (see FIG. 3). The first location of detection was in good agreement with the location of ferrocene and thiophene decomposition. The bulk nucleation and detection of nanoparticles occurred only after thiophene decomposed. Downstream measurements showed an almost immediate disappearance of particles at ~1200° C.

SMPS measurements of particle size distribution showed an onset of formation at 200 mm which corresponds to a tubular reactor wall temperature of ~960° C. Nucleated particles appeared with a particle size of about 4 nm. It is likely that the sampling method did not retroactively correct for all losses of small particles. Moving from 200 mm to 300 mm, the particle concentration and diameter grew. The peak of particle concentration was $7 \times 10^8$ #/$cm^{-3}$ at ~1100° C. for the 1150° C. tubular reactor and $10 \times 10^8$ #/$cm^{-3}$ at ~1100° C. for the 1300° C. tubular reactor. After the peak particle concentration, the measured particle diameters decreased as the temperature increased towards the hottest zone indicating potential particle-to-gas conversion ie evaporation. This trend was strongly temperature dependent and led to almost complete particle evaporation at a set point of 1300° C. For lower set points, the concentration of hydrogen-carried catalyst nanoparticles remained high. The maximum particle concentration occurred at a set point of 1300° C. and the lowest was measured at 1150° C. Regardless of the set points, the highest temperatures corresponded to the lowest particle concentrations.

Figure 4:
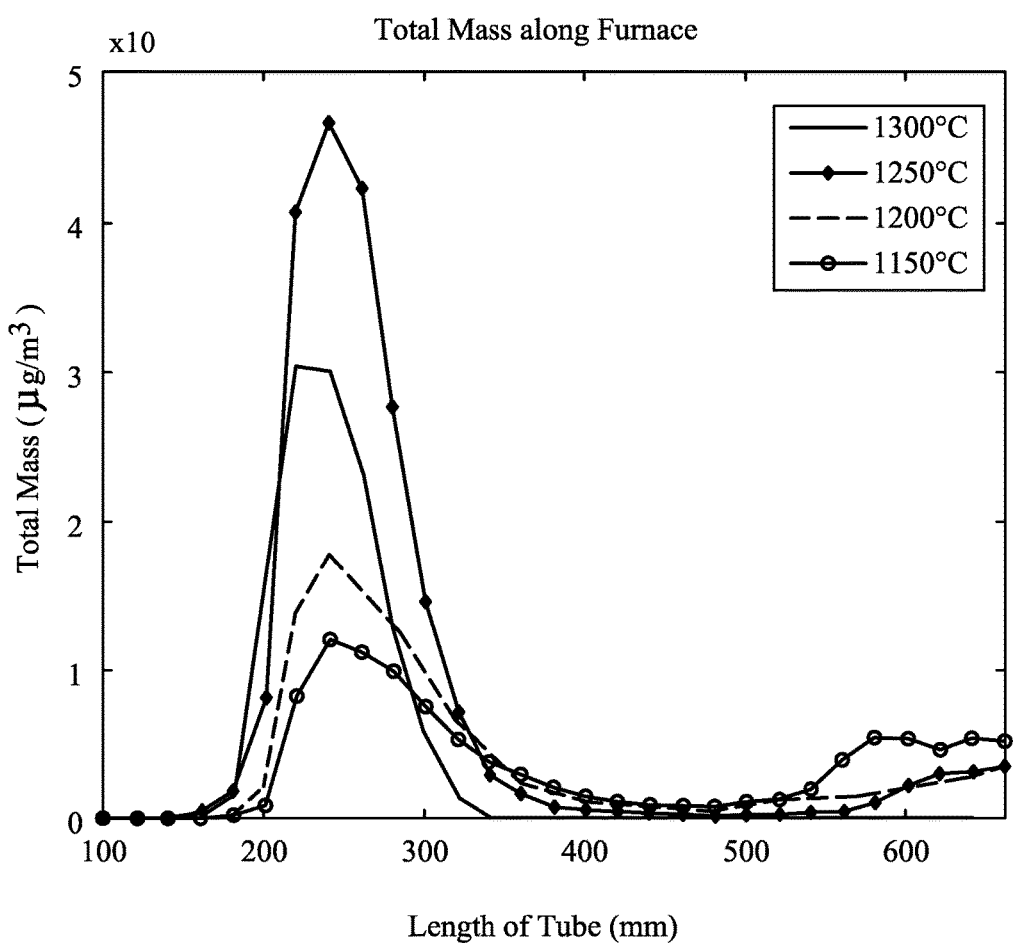
FIG. 4 illustrates the total mass of catalyst nanoparticles along the tubular reactor.

As the temperature fell downstream from the maximum, re-nucleation occurred which resulted in an increase in particle concentration but to a concentration less than the concentration which was observed upstream. At a set point of 1250° C., the total mass was at a maximum which indicates that at higher set point temperatures, evaporation is competing with decomposition, nucleation and coagulation (see FIG. 4).

CNT Formation and Particle Size Distributions

Samples of the CNT fibre formed in experiments with methane as a source of carbon were taken along the axis of the tubular reactor. SEM images revealed different morphologies of the CNT fibre along the axis (see FIG. 5). The fibre extended through the tubular reactor and attached to the wall where ferrocene decomposed and thiophene started to decompose at ~170 mm which corresponds to a temperature of ~700° C. At the beginning of the tubular reactor were found CNT bundles (diameter 15-35 nm) and individual CNTs mainly oriented along the gas flow. Some catalyst nanoparticles were attached to these small CNT bundles close to the entrance. The first CNTs that started to grow in the zone of ferrocene decomposition showed only some attached nanoparticles. The carbon for CNT formation in this region is likely to be coming from the thermal breakdown of ferrocene and catalytic decomposition of methane. As the temperature increased, there was more ferrocene and thiophene break down and the initially grown CNTs act as a surface for heterogeneous nucleation of nanoparticles. CNT growth and nanoparticle nucleation occur in parallel. Bundling and branching of CNTs due to Van der Waals forces were observed. Many nanoparticles were found in between CNTs and bundle-junctions. Nanoparticles attached to CNTs and CNT bundles might act as a catalyst and growing point for further CNT growth.

The fibre further downstream the axis of the tubular reactor showed almost no attached catalyst nanoparticles. The nanoparticles disappeared as the temperature increased indicating particle evaporation. Some nanoparticles attached to initially grown CNTs potentially catalyze further CNT growth. As the temperature dropped downstream from the maximum temperature, re-nucleation occurred resulting in an increase in impurities in the web whereas the fibre in and just before the hottest zone appears to be nearly free of impurities and catalyst nanoparticles. The bulk CNT web formed near the exit had impurities and catalyst nanoparticle clusters were present. Since carbon is mainly available upstream from ferrocene and thiophene decomposition, carbon from methane only becomes available as the temperature rises and when catalyst nanoparticles start to evaporate. Once re-nucleation of nanoparticles occurs as the temperature drops, there is observed a bulk formation of CNTs from decomposed methane present alongside re-nucleated catalyst nanoparticles.

Overview of Results

Experiments with just a single reactant (ferrocene, thiophene or methane) reveal that a first wall deposit is related to ferrocene decomposition and a second one to thiophene decomposition. The simulated ferrocene decomposition along the centreline of the tubular reactor according to $$\frac{DC}{Dt} = D_c \nabla^2 C - k_c C e^{-E_a/(R_u T)}$$

is in good agreement with experimental observations and matches the location at which iron can be detected as a deposit at the tubular reactor wall.

A simulation including surface growth and coagulation of iron based nanoparticles along the centreline shows the evaporation of nanoparticles. A first particle size distribution measured at a temperature set point of 1200° C. and ~1100° C. (240 mm) is where the total mass of airborne nanoparticles is at a maximum. A second particle size distribution measured at ~700° C. (540 mm) is where re-nucleation and surface growth occurs as the temperature drops. The first and second particle size distribution are used as an input for the simulation. At these locations a saturation ratio of S=actual monomer concentration/saturation concentration of monomers=1 is assumed.

A snapshot of the process including methane as a carbon precursor shows the continuous CNT fibre reaching through almost the entire tubular reactor. Further downstream where the temperature drops after the hottest zone, the fibre is attached to the bulk CNT web. In the middle of the tubular reactor, the fibre is partly attached to the wall. Resistance measurements between the tubular reactor wall and the exit were carried out after the fibre which reached through the tubular reactor was taken out (see FIG. 6). Starting near the hottest zone, the wall becomes conductive indicating a CNT coating at the wall. Microscopy analysis of material gained from the wall confirmed these results. In this region, methane thermally decomposes and most of the carbon becomes available. At the same time, particle measurements showed that the catalyst nanoparticles evaporate and are no longer available to catalyze CNT growth.

Conclusions

Particle size distributions along the axis of the tubular reactor show a distinctive, temperature dependent appearance and disappearance of catalyst nanoparticles. Four specific regions of CNT web production showing different structural features that directly correlate to the nanoparticle behavior have been confirmed using SEM imaging. At the beginning of the reaction zone, homogeneous nanoparticle nucleation in a carbon-lean environment stimulates the growth of CNT material with a low impurity profile. This is followed by a region characterised by a higher impurity concentration where there is a contribution from heterogeneous nucleation of catalyst particles on the existing CNT structures and agglomeration of nanoparticles. The lowest impurity concentration is seen in the hottest zone of the tubular reactor where non-encapsulated nanoparticles evaporate. Towards the exit, the decrease in temperature profile stimulates the re-nucleation of iron-based nanoparticles from a saturated vapour in a carbon rich environment which leads to a rapid increase in the growth of carbon nanostructures which is dominated by undesirable impurities. To eliminate the possibility that re-nucleation is an aberration caused by the closed system, an experiment was carried out in an open-ended system and showed similar results.

As shown by IR data and the location of deposits on the quartz tubular reactor walls, ferrocene and thiophene decompose independently within narrow temperature dependent zones indicating that the onset of decomposition for each is thermally rather than catalytically driven.

EXAMPLE 2

Figure 10:
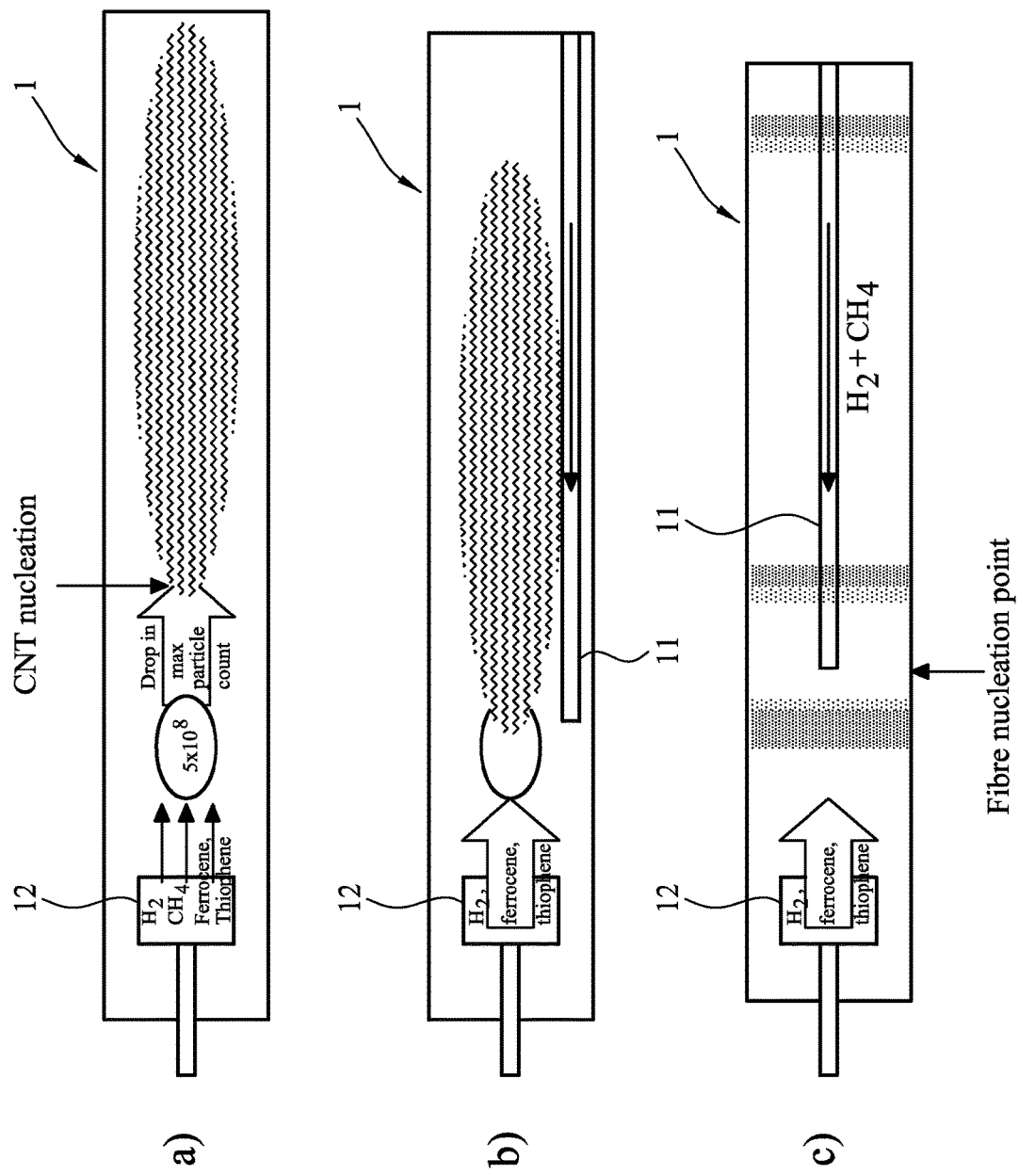
FIG. 10 illustrates a tubular reactor operated (A) conventionally and (B-C) in accordance with embodiments of the method of the invention.

(A) FIG. 10A illustrates a tubular reactor 1 operated conventionally to introduce hydrogen, ferrocene and thiophene via injector 12 at the downstream end. Methane and hydrogen were introduced at the upstream end. CNT growth was determined by locating the position at which a sample probe was blocked. The onset of CNT nucleation (the fibre nucleation point) occurred downstream from a region of peak particle concentration ($5 \times 10^8$) and from an incubation region over which the particle count fell.

(B) FIG. 10B illustrates a tubular reactor 1 operated according to an embodiment of the method of the invention. In this embodiment, a counterflow of hot methane and hydrogen was released into the region of peak particle concentration using a lance 11 inserted into the tubular reactor 1. A flow rate of 19 to 45 cm$^3$/min was sufficient for the growth of CNTs to occur in the region of peak particle concentration. A flow rate of 45 to 55 cm$^3$/min moved the growth of CNTs into a low temperature zone and closer to the injector 12.

(C) FIG. 10C illustrates a tubular reactor operated according to an embodiment of the method of the invention. In this embodiment, a counterflow of hot methane and hydrogen was released at the fibre nucleation point.

The experimental setup was as follows:
Quartz tube 50 mm OD, 46 mm ID, 1200° C. set point, Carbolite STF 15/180
Showerhead injector 85 mm into tube
Ferrocene 75 C, 40 sccm in $H_2$
Thiophene 0.1 C, 10 sccm in $H_2$
$CH_4$ (40 sccm) supply line entering through centre port on exit flange, through ¼" OD alumina line whose tip is positioned 20 cm from tube entrance
$CH_4$ diluted 1:4 with $H_2$ (160 sccm $H_2$+40 sccm $CH_4$) with the dilution happening at the entrance to the ceramic tube to limit $CH_4$ breakdown in the counterflow alumina line
Showerhead: 340 sccm $H_2$+40 sccm $H_2$/Fe+10 sccm $H_2$/thiophene
Total flow through tubular reactor: 590 sccm.

The experimental protocol was as follows:
11:30—Flush with $H_2$ (340 sccm entrance, 160 sccm counterflow)
11:33—Start Fe (40 sccm) and thiophene (10 sccm) through showerhead (pause for ~1 min)
11:40—Start $CH_4$ 40 sccm counterflow
11:47:34—CNT web formed in a third zone and reached the exit
11:50:00—Switched off all reagents, 10 sccm Ar through injector and counterflow line, heat off. Ferrocene heat off. Once tubular reactor had reached ~80° C., the entrance flange was removed and the tubular reactor was extracted with the counterflow line still in place.

FIG. 11a illustrates the results from this embodiment of the method of the invention compared with results from the conventional method (see FIG. 11b-c). In FIG. 11a, the counterflow of methane and hydrogen encouraged the growth of CNT material in a short time span (5 minutes) over which the conventional method produces no fibre. The downstream depositions in the method of the invention (FIG. 11a) are less dense than those of the conventional method (FIGS. 11b-c).

EXAMPLE 3

According to an embodiment of the method of the invention illustrated schematically in FIG. 12, a 10 sccm counterflow of thiophene was released into the region of the tubular reactor (R) in which re-nucleation occurred. The effect on the particle distribution and concentration was studied. Methane was subsequently introduced to see how the counterflow of thiophene affects fibre generation compared with the conventional arrangement.

The experimental setup was as follows:
Alumina tube reactor 50 mm OD, 40 mm ID
Set point 1200° C.
Insulation: same as that used with previous quartz runs to keep temperature profile as similar as possible
Showerhead injector
Particle sampling probe: 3 mm OD alumina (1.9 mm ID) through the centre port of the exit flange, 16/1000 critical orifice
Counterflow thiophene: alumina tube inserted through exit port so that the tip was 25 cm from the exit of the tubular reactor just upstream from region R.

Thiophene appears to condition re-nucleating catalyst particles for CNT growth. After five minutes flow of methane, a visual inspection revealed that a thick web-cap had formed and fibre appeared down the length of the tubular reactor. The thread looked thicker than that formed with no counterflow of thiophene and particulates were visible along the thread.

EXAMPLE 4

An experiment was carried out to determine whether narrowing the diameter of the tubular reactor towards the discharge outlet led to a change in flow velocity to assist the retrieval of the CNT material as a sock.

In the necked arrangement shown in FIG. 13a, an experiment in which different lengths extended beyond the tubular reactor showed that a CNT sock could be generated in a 28 mm diameter tube with lower reagent feed rates to permit the sock to be withdrawn upstream of the third zone.

In the trumpet arrangement shown in FIG. 13b, an experiment in which different lengths extended beyond the tubular reactor showed that a CNT sock could be generated in a 50 mm diameter tube to permit the sock to be withdrawn upstream of the third zone.

The invention claimed is:
1. A method for the production of carbon nanotube structures comprising:
(a) introducing a flow of metal catalyst or metal catalyst precursor into a temperature-controlled flow-through reactor;
(b) exposing the flow of metal catalyst or metal catalyst precursor to a first temperature zone sufficient to generate particulate metal catalyst, wherein the first temperature zone includes a region of peak particle concentration;
(c) releasing an axial or radial flow of a source of carbon into the temperature-controlled flow-through reactor at a release point;
(d) exposing the particulate metal catalyst and source of carbon to a second temperature zone downstream from the first temperature zone, wherein the second temperature zone is sufficient to produce carbon nanotube structures;
(e) exposing the particulate metal catalyst and source of carbon to a third temperature zone downstream from the second temperature zone, wherein the third temperature zone is sufficient to evaporate the particulate metal catalyst;
(f) exposing the particulate metal catalyst and source of carbon to a fourth temperature zone downstream from the third temperature zone, wherein the fourth tempera- ture zone is sufficient to re-nucleate the particulate metal catalyst and to produce carbon nanotube structures; and (g) discharging the carbon nanotube structures from a discharge outlet of the temperature-controlled flow-through reactor, wherein the release point is substantially between the beginning of the first temperature zone and the end of the second temperature zone and the method further comprises: (f') releasing an axial or radial flow of a source of sulphur into the temperature-controlled flow-through reactor at a release location, wherein the release location is at or near to the fourth temperature zone;

wherein the first temperature zone sufficient to generate particulate metal catalyst extends over at least the range 600 to 1100° C. and the first temperature zone is in a first reaction chamber of the temperature-controlled flow-through reactor;

the second temperature zone sufficient to produce carbon nanotube structures extends over at least the range 900 to 1150° C. and the second temperature zone is in a second reaction chamber of the temperature-controlled flow-through reactor;

the third temperature zone sufficient to evaporate the particulate metal catalyst extends over at least the range 1150 to 1400° C. and the third temperature zone is in a third reaction chamber of the temperature-controlled flow-through reactor; and the fourth temperature zone sufficient to re-nucleate the particulate metal catalyst and to produce carbon nanotube structures extends over at least the range 600 to 1150° C. and the fourth temperature zone is in a fourth reaction chamber of the temperature-controlled flow-through reactor.

2. The method as claimed in claim 1 wherein the release point is substantially coincident with the region of peak particle concentration.

3. The method as claimed in claim 1 wherein the release location is upstream from and near to the fourth temperature zone.

4. The method as claimed in claim 1 wherein the temperature profile in the temperature-controlled flow-through reactor is substantially parabolic.

5. The method as claimed in claim 1 wherein in step (c), the source of carbon is released in an axial counterflow.

6. The method as claimed in claim 1 wherein in step (c) the source of carbon is released radially.

7. The method as claimed in claim 1 wherein the source of carbon is methane optionally in the presence of an optionally substituted and/or optionally hydroxylated aromatic or aliphatic, acyclic or cyclic hydrocarbon which is optionally interrupted by one or more heteroatoms.

8. The method as claimed in claim 1 wherein the metal catalyst is iron.

9. The method as claimed in claim 1 wherein the metal catalyst precursor is a sulphur-containing organometallic.

10. The method as claimed in claim 9 wherein the metal catalyst precursor is ferrocene and a sulphur-containing ferrocenyl derivative.

11. The method as claimed in claim 1 wherein the metal catalyst or metal catalyst precursor is introduced in step (a) together with a sulphur-containing additive.

12. The method as claimed in claim 11 wherein the metal catalyst precursor is ferrocene optionally together with a sulphur-containing additive being thiophene or carbon disulphide.

13. The method as claimed in claim 1 wherein the source of sulphur is thiophene or carbon disulphide.

14. The method as claimed in claim 1 further comprising: measuring the particle size distribution of the particulate metal catalyst in the first temperature zone.

15. The method as claimed in claim 1 further comprising: measuring the particle size distribution of the particulate metal catalyst in the fourth temperature zone.

* * * * *